United States Patent [19]

Disharoon

[11] 4,317,401

[45] Mar. 2, 1982

[54] METHOD AND APPARATUS FOR MICROTOMY

[76] Inventor: Dale R. Disharoon, 2480 Newcastle Ave., Cardiff, Calif. 92007

[21] Appl. No.: 201,131

[22] Filed: Oct. 27, 1980

Related U.S. Application Data

[62] Division of Ser. No. 56,469, Jul. 11, 1979, Pat. No. 4,269,092.

[51] Int. Cl.³ .............................................. G01N 1/06
[52] U.S. Cl. ....................................... 83/856; 30/350; 76/101 R; 83/701; 83/915.5; 225/2
[58] Field of Search .............. 83/651, 856, 701, 915.5; 76/101 R; 30/350; 225/2

[56] References Cited

U.S. PATENT DOCUMENTS 3,803,958 4/1974 Fernandez-Moran ......... 83/915.5 X
4,051,755 10/1977 Raveed ........................... 83/915.5 X Primary Examiner—James M. Meister
Attorney, Agent, or Firm—Fitch, Even, Tabin, Flannery & Welsh

[57] ABSTRACT

Methods and apparatus for microtomy utilizing a vitreous carbon knife element having particular properties. The knife element may desirably be rendered hydrophilic along at least one surface to facilitate cleaved sample processing, and provides for economical, high quality cleaving of multiple tissue samples.

10 Claims, 7 Drawing Figures

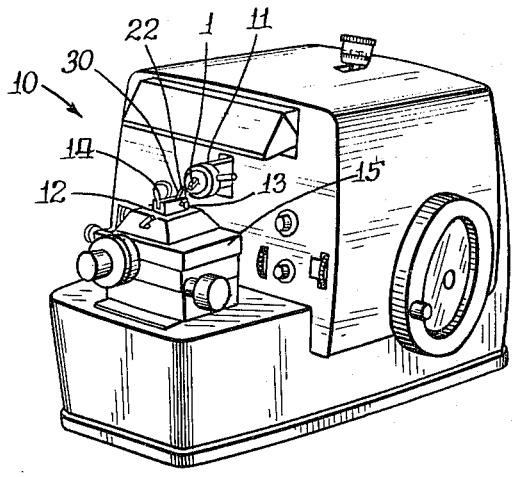
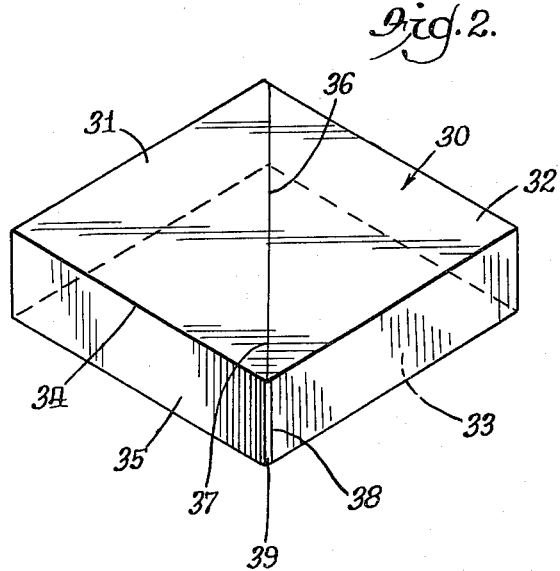
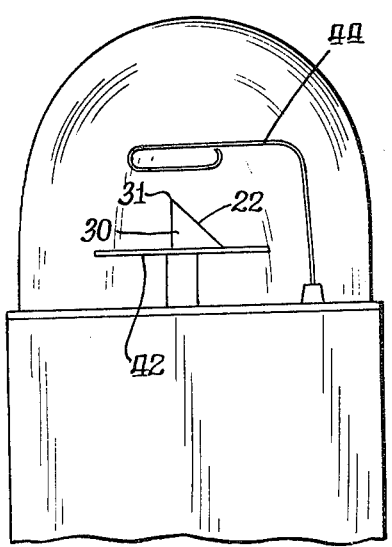
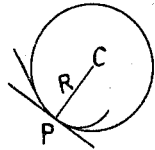

METHOD AND APPARATUS FOR MICROTOMY

This is a division, of application Ser. No. 56,469, filed July 11, 1979, now U.S. Pat. No. 4,269,092.

The present invention is directed to microtomy methods and apparatus, and, more particularly, is directed to methods and apparatus for sectioning of specimen materials such as tissue samples for microscopic examination.

The main principles of ultramicrotomy were adapted from light microscopy. However, major modifications had to be made with respect to embedding procedures, the manufacture of knives and the construction of microtomes. Much of this development has been the result of empirical work and many details of well known steps in conventional sectioning procedures are not fully understood in theory.

In conventional sectioning procedures for sample sectioning, frozen tissue samples, or tissue samples embedded in either a rigid or semi-solid organopolymeric matrix are rapidly cleaved by means of a microtome sectioning knife. In order to produce sections of specimen suitable for ultramicroscopic examination, marks on the specimen due to knife edge defects or deformations, should be minimized, and the knife edge should function to cleave the specimen cleanly. The quality of microtome sections depends to a large extent on the quality and characteristics of the microtome knife, and the cutting process is also influenced by properties of the trough fluid used in the sectioning and sectioned sample transport operations.

Metallic knives such as steel microtome knives were originally used for cutting sections for ultramicroscopic examination by techniques such as electron microscopy. However, the use of steel microtome knives in cutting sections for electron microscopes has substantial disadvantages, especially in the achievement of satisfactory sample surfaces of examination and in the provision and maintenance of sufficiently sharp knife edges. Substantial effort has been expended in the art to overcome such difficulties and to provide cutting methods utilizing materials having suitable homogeneity and hardness without excessive brittleness. One significant result of such development efforts has been the provision of cleaving methods for providing and using glass "knives" by breaking glass sheets to produce a cleaved cutting edge [Latta, et al., *Use of a Glass Edge in Tissue Sections for Electron Microscopy*, Proc. Bio. Med, Vol. 74, pp. 436–439 (1950)]. By providing a series of straight parallel scorings at 90° to the long axis of a glass strip, with one central portion of each 2" distance kept free of score marks, 1" glass blocks may be produced that can then be cleaved at a 45° angle (to score-mark free corner) thus producing a knife edge length along the thickness dimension of one surface of one triangle (1"×1"×¼") and a less perfect edge on one edge of the opposite triangle. However, while such glass knives represent a substantial improvement in the art, such cleaved edges can be used only for a limited time, and for providing a limited number of sectioned samples.

In view of the tendency of such cleaved edges to lose their properties with time and/or use, glass microtome knives are conventionally made on site as needed under conditions of use. In this latter connection, specific jigs have been developed for producing precision glass knives for laboratory applications, specifically for cleaving tissue samples for microscopy. Examples of such devices are disclosed in U.S. Pat. Nos. 3,207,398, 3,494,521 and 3,908,878.

The use of glass knives in microtomy suffer from a number of disadvantages. They may be time consuming to produce and, because glass is physically a super cooled liquid, have a very short life. The cleaved edges produced by the intersection of the fracture plane with another plane at a score-free junction may be sharp initially, but within a matter of hours and without use, the edge will begin to dull due to flow characteristics of the glass, and/or its inability to maintain the precise molecular arrangement that exists at the cleaving edge immediately after breaking. Such knives, as indicated must therefore be produced at the point of application since their structural longevity is no more than a day or two in their sharpest state. In addition to such limitation, glass knives dull quickly in use and may be utilized only with difficulty in providing numerous thick sections of hard specimens including routinely embedded materials.

In this regard, not only is it desirable to produce thin sections of hard samples, it is frequently desirable to prepare samples for ultramicroscopic examination by cleaving relatively thick sections of the specimen material embedded in an organopolymeric material, such as a specimen having a thickness in the range of 10 to 50 microns, and to reorient and reembed the thick specimen at a different angle. The reembedded specimen may then be subsequently sectioned to provide the desired specimen. Glass knives function best when cleaving sections no more than 2 microns in thickness, but may be utilized to provide a very limited number of sections per knife when a thickness of about 2 to about 10 microns is desired. Thicker sections may not be reliably be provided through the use of glass knives.

In an attempt to overcome the general thin and thick sectioning limitations of glass knives, knife edges of harder crystalline materials such as diamond have been proposed for microtomy purposes [Fernandez-Moran, H. A., *A Diamond Knife for Ultra Thin Sectioning*, Exp. Cell Research, 5, pp. 255–256 (1953)], and subsequently have achieved substantial commercial application. However diamond knives are very expensive and difficult to produce thereby limiting their general applicability. Further, diamond knife edges are fragile, and sensitive to impacts and small blows, so that a knife being used for thick sectioning has a shorter life than one being used for thin sectioning. The economic risk of various sample materials represents a substantial limitation in the use of diamond knives.

Because of the expense and fragility of diamond knives, various efforts have been made to improve the cutting qualities and longevity of relatively inexpensive glass knives. For example, efforts have been made to coat glass knives with materials such as tungsten in an effort to overcome deficiencies of glass [Roberts, *Tungsten Coating— A Method of Improving Glass Microtome Knives for Cutting Ultrathin Sections*, Journal of Microscopy, Vol. 103, Pt. 1, pp. 113–119 (1974)]; but such techniques have not achieved wide acceptance. Still others [Ward, *Some Observations on Glass Knife Making*, Stain Technology, Vol. 52, pp. 305–309 (1977)], have tried varying the bevel angle, up to 55°, of the glass knife edge to enhance cleaving capabilities, but succeed only to a limited degree.

However, despite significant need for improved microtomy methods and apparatus, there have been few significant developments in respect of glass microtomy knives since their introduction in 1950, and glass and diamond microtomy systems remain as the two principal alternatives available for ultramicroscopic sample sectioning.

Accordingly, there is a need for improved methods and apparatus for specimen sectioning, and it is an object of the present invention to provide such methods and apparatus. It is a further object to provide methods and apparatus for microtomy which permit the cleavage of a relatively large number of samples from a single, relatively inexpensive knife edge without the need for the frequent manufacture of new knife edges common to methods utilizing cleaved glass knives. It is another object of the present invention to provide such methods and apparatus for providing relatively thick specimen sections as well as thin specimen sections.

These and other objects of the invention will become apparent from the detailed description and accompanying drawings of which:

FIG. 1 is a perspective view of microtome apparatus utilizing a knife element in accordance with the present invention;

FIG. 2 is a perspective view of the knife element of the microtome of FIG. 1 and another similar element following a controlled fracture step in the manufacture of such elements;

FIG. 3 is a schematic illustration of the knife element of the microtome of FIG. 1, in a manufacturing step subsequent to the fracture step illustrated in FIG. 2.

FIG. 7 is a diagram for describing radius of curvature determination.

Figure 4:
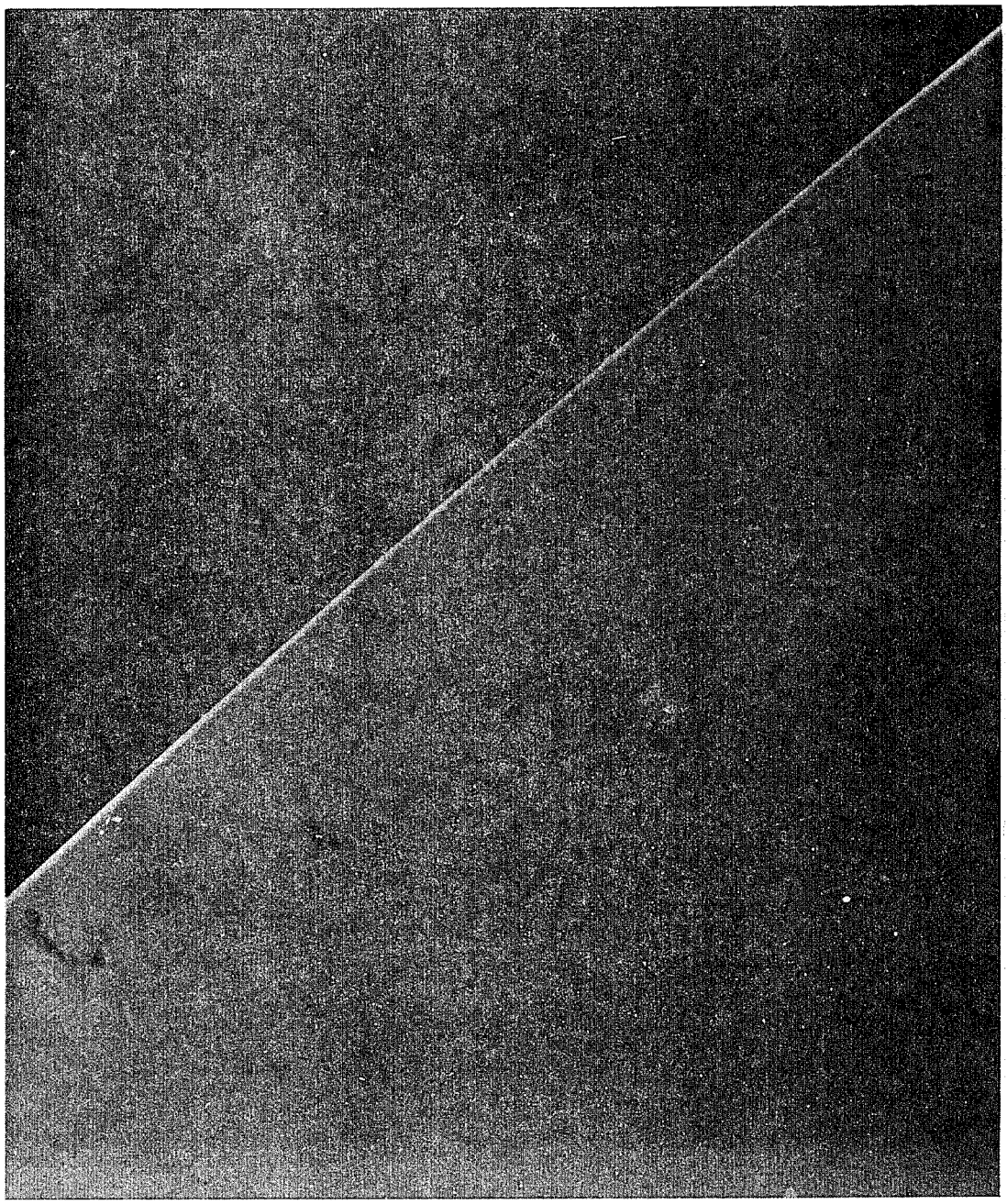
FIG. 4 is a photograph by scanning electron microscope of a portion of the cutting edge of the vitreous carbon knife element of FIG. 1 at a magnification of 540.

Generally in accordance with the present invention, methods and apparatus for cleaving specimen materials for microscopic examination are provided utilizing microtome knife elements of particular design and composition, as well as methods of manufacture of such vitreous knife elements.

In this connection, microtome knife elements are provided in accordance with the present invention which comprise a vitreous carbon body of particular physical property parameters, and having two intersecting substantially plane surfaces which intersect along a substantially linear intersection edge. The plane surfaces should best intersect at an angle in the range of from about 35° to about 60°, and preferably in the range of from about 40° to about 50°, to form a high performance microtome knife edge. At least one of the intersecting plane surfaces adjacent the microtome knife edge may be provided with a hydrophilic surface, as will be described in more detail hereinafter. As indicated, the microtome knife element utilized in accordance with the present invention comprises a vitreous carbon body. Though polymeric carbon is a better term for this material, due to some of this carbon's properties it has been designated vitreous carbon. The vitreous carbon should best be an isotropic for certain manufacturing procedures for microtome knives involving controlled fracture of the material.

Vitreous carbon is a nongraphitic carbon material which may be formed by controlled heating of selected polymeric precursors in accordance with known procedures which generally involve slow carbonization of a formed article under conditions which permit diffusion of pyrolysis products without disruption of the physical integrity of the artifact, and which is generally accompanied by a larger, but predictable contraction in the size of the formed artifact [Jenkens, et al., *Polymeric Carbons—Carbon Fibre, Glass and Char,* Cambridge University Press (1976)]. Vitreous carbon may be produced in a variety of forms, and is desirably produced in a molded sheet form. The molecular structure of the vitreous carbon is believed to involve carbon atoms joined by strong covalent bonds to form relatively small planar hexagonal arrays plus other carbon arrays which are disordered with respect to one another in a turbostratic structure.

The existence of a cross-linked aromatic structure in the original polymer, or during thermal degradation is believed to prevent formation or rearrangement to a full graphite structure on subsequent heating and provides for the turbostratic structure.

Vitreous carbon knife elements in accordance with the present invention should generally be provided from vitreous carbon material having a density of at least about 1.35 g/cc$^2$ and typically have a bulk density of about 1.45 g/cc$^2$. The density will generally be less than about 1.5 g/cc$^2$, but it should be noted that the inclusion of carbide forming elements may increase the density of a vitreous carbon material.

The physical properties of the vitreous carbon material are important in the provision of microtome knives. In this connection, the vitreous carbon should have a compressive strength of at least about 90,000 pounds per square inch, and will generally be in the range of from about 90,000 to about 140,000 pounds per square inch. The vitreous carbon should also have a tensile strength of at least about 25,000 pounds per square inch, and will generally be in the range of from about 25,000 to about 35,000 pounds per square inch at 20° C. The material should further have a Young's modulus of at least about $3 \times 10^6$ pounds per square inch (e.g., in the range of $3$–$4 \times 10^6$ psi), and a hardness of at least about 7 on mohs scale. Accordingly, the vitreous carbon material utilized in the knife elements herein is a very hard material which will scratch most forms of siliceous glass. It is further important that the vitreous carbon be highly uniform in structure, and in this connection should best be free of crystalline inclusions, porosity or other structural defects. In this connection, the vitreous carbon should best have a permeability of less than about $2.5 \times 10^{-11}$ cm$^2$/sec (helium) and a porosity of less than about 0.05. The vitreous carbon materials should be substantially nongraphitic and homogenous in composition and in this connection, the x-ray crystallite size $L_c$ of the vitreous carbon should best be less than about 26 Å and more preferably less than about 24 Å. The thermal conductivity of the vitreous carbon may desirably be at least about 0.01 cal/cm.sec.°C.

As indicated, the vitreous carbon used for knife manufacture by fracture methods is desirably substantially free of crystalline defects, and in this connection, it is desirable to use very high purity polymer precursors which are substantially free of components which induce or provide carbon (graphite) or carbide crystallization. However, the vitreous carbon may be reacted with various carbide forming elements to modify the properties of the vitreous carbon. Such reaction may be carried without substantial graphite formation and the materials may be combined within the turbostratic structure of vitreous carbon without merely forming an external deposit. In this regard, a vitreous carbon knife element may be reacted with carbide forming elements such as silicon, boron, tungsten, tantalium, titanium, zirconium, hafnium, vanadium, niobium, chromium, molybdenum, and mixtures thereof without substantial change in the shape of the knife edge, by selecting a volatile compound (such as hydride) of the carbide forming elements and reacting this compound in the vapor phase with the vitreous carbon microtome knife at a suitably elevated temperature.

Turning now to the drawings, various aspects of the present invention will be more particularly described with respect to the microtome apparatus illustrated in FIG. 1. The apparatus 10 is of generally conventional design comprising an object holder assembly 11 adapted to secure a specimen 1 for sample preparation. The microtome apparatus 10 further comprises a knife holder assembly 12 of conventional design of the type utilized for holding glass and diamond knife elements, and which is adapted to secure in mounted relationship thereto an unconventional knife element 30 of particular specification in accordance with the present invention. The illustrated holder assembly 12 comprises a steel yoke 13 with a soft plastic blunt end which rests against the knife, and provides a slot 14 at its midpoint which is sufficiently wide to accomodate the thickness of the vitreous carbon knife element 30. The vitreous carbon knife element is mounted in the holder assembly 12 between the yoke 13 and knife slot 14 and held in alignment with the yoke 13 when tightened. The knife holder 12, with the vitreous carbon knife in place, is then placed in final knife angle adjustment by being secured to 15 of the ultra microtome. The illustrated vitreous carbon knife element has a substantially linear knife edge 31 of extreme sharpness which has exceptional capacity for sample cleavage. In the illustrated embodiment 10, at least one plane surface 22 of the knife 30 is rendered hydrophilic and a water trough is provided along the surface 22 to float cleaved sample sections off the edge of the knife in accordance with conventional practice.

In operation, the object holder is moved toward the knife element 30 and the sample impacts the knife edge 31 to cleave sample tissues from the sample object.

The sample may be of the organopolymeric impregnated type in which a tissue specimen has diffused thereinto an organopolymeric precursor such as an acrylic monomer or epoxy resin precursor, which is subsequently polymerized to provide a rigid and relatively hard sample specimen for cleavage. The forcing of the object against the edge of the knife element 30 may generate immense pressures and mechanical strains at the knife edge, and the knife 30 must be capable of repeatedly withstanding such conditions. While individual knife elements vary, such conditions normally would require the changing of a cleaved glass knife element after, for example, less than about 10 specimen sample sections of conventional thickness in a range of less than 2 microns and about 5 microns of 2-10 microns thickness. Substantial difficulty may be experienced with conventional glass knifes in efforts to cleave samples of greater thicknesses, such as from about 10 to 50 microns in thickness. However, the vitreous carbon knife element 30 readily and repeatedly cleaves relatively thick organopolymeric impregnated specimen samples in the range of from about 10 to 50 microns of thickness and is utilizable in the cleavage of a relatively large number of specimens, for example, in excess of 100 specimens without a change in quality.

As indicated, the knife elements provided in accordance with the present invention are manufactured of vitreous carbon, and may be provided using slightly modified equipment similar to that used in the manufacture of glass microtome knife elements. In this connection, the microtome knife elements may be manufactured by providing a suitable vitreous carbon sheet having substantially flat parallel surfaces, scoring the sheet along a first line, fracturing the sheet along the first line orthogonally to the parallel surfaces to form a first substantially flat cleaved surface, scoring the sheet along a second line intersecting the first scored line and fracturing the sheet along the second line to form a substantially flat cleaved surface orthagonal to said sheet surface, free of score marks and intersecting the first cleaved surface to form a microtome knife edge.

FIG. 2 illustrates in perspective view the knife element 30 which has been broken from a scored vitreous carbon plate 31 having flat, smooth, parallel surfaces 32, 33 and which has previously been fractured along a line 34 to form a substantially planar fracture surface 35 perpendicular to the surfaces 32, 33. The plate 31 is provided from a commercially available VITRECARB vitreous carbon sheet having a thickness of 0.25 inch and a length of about 2 cm. which is manufactured by Fluorocarbon Company of Anaheim, Calif. and has a density of 1.47 g/ml, a permeability of less than $2.5 \times 10^{-11}$ cm$^2$/sec, a porosity of less than 0.05 percent, a thermal conductivity in the range of 0.01 to 0.02 cal/cm/sec/°C., a compressive strength in the range of 90,000 to 140,000 psi, a tensile strength in the range of 25,000 to 35,000 psi at 20° C., and a Young's modulus of $3-4 \times 6^{10}$ psi. The plate 31 is substantially pure carbon (about 2 ppm impurities) which is substantially free of crystalline carbide inclusions.

The plate 31 is fractured along diagonal score line 36 to form a fracture plane 37 which provides a microtome knife edge 38 at its intersection with the fracture plane 35 and leaving a shelf 39 on the opposite triangle. The angle formed by the intersection of the fraction planes 35, 37 is typically in the range of from about 45° to about 55°, but may be varied within a broad range. The intersection 38 of the fracture planes 35, 37 forms an extremely sharp substantially linear edge, which has a radius of curvature of less than about $5\mu$. By radius of curvature is meant, the radius of curvature R of a plane curve at any point P (FIG. 7) is the distance, measured along the normal, on the concave side of the curve, to the center of curvature, C, this point being the limiting position of the point of intersection of the normals at P and a neighboring point Q, as Q is made to approach P along the curve.

While the illustrated knife edge 38 is manufactured by cleavage techniques as previously described, vitreous carbon microtome knives may be provided by grinding and lapping procedures and polished to produce a very sharp and substantially linear knife edge.

Figure 5:
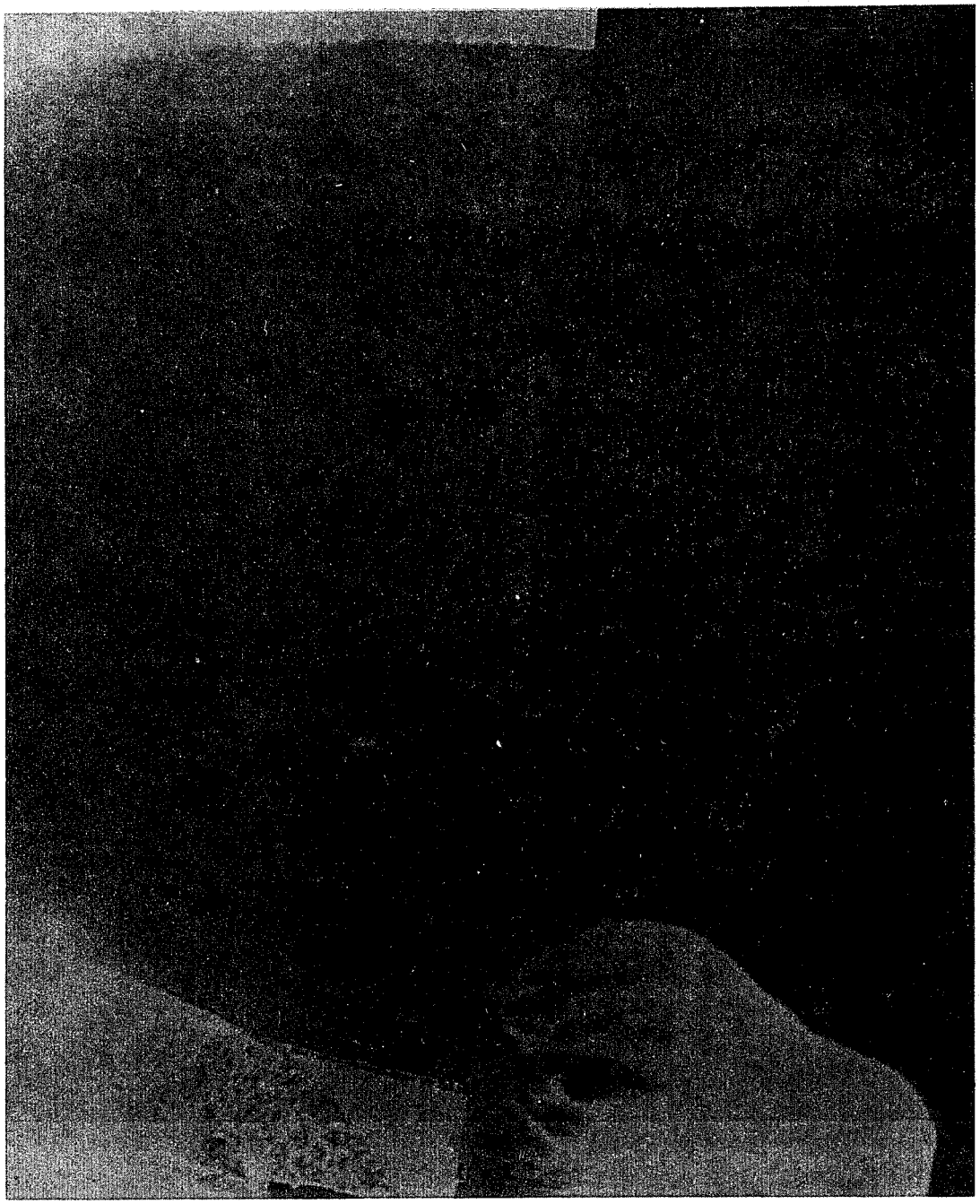
FIG. 5 is a photograph by scanning electron microscope of the cutting edge of a vitreous carbon microtome knife element produced by machining, at a magnification of 27.
Figure 6:
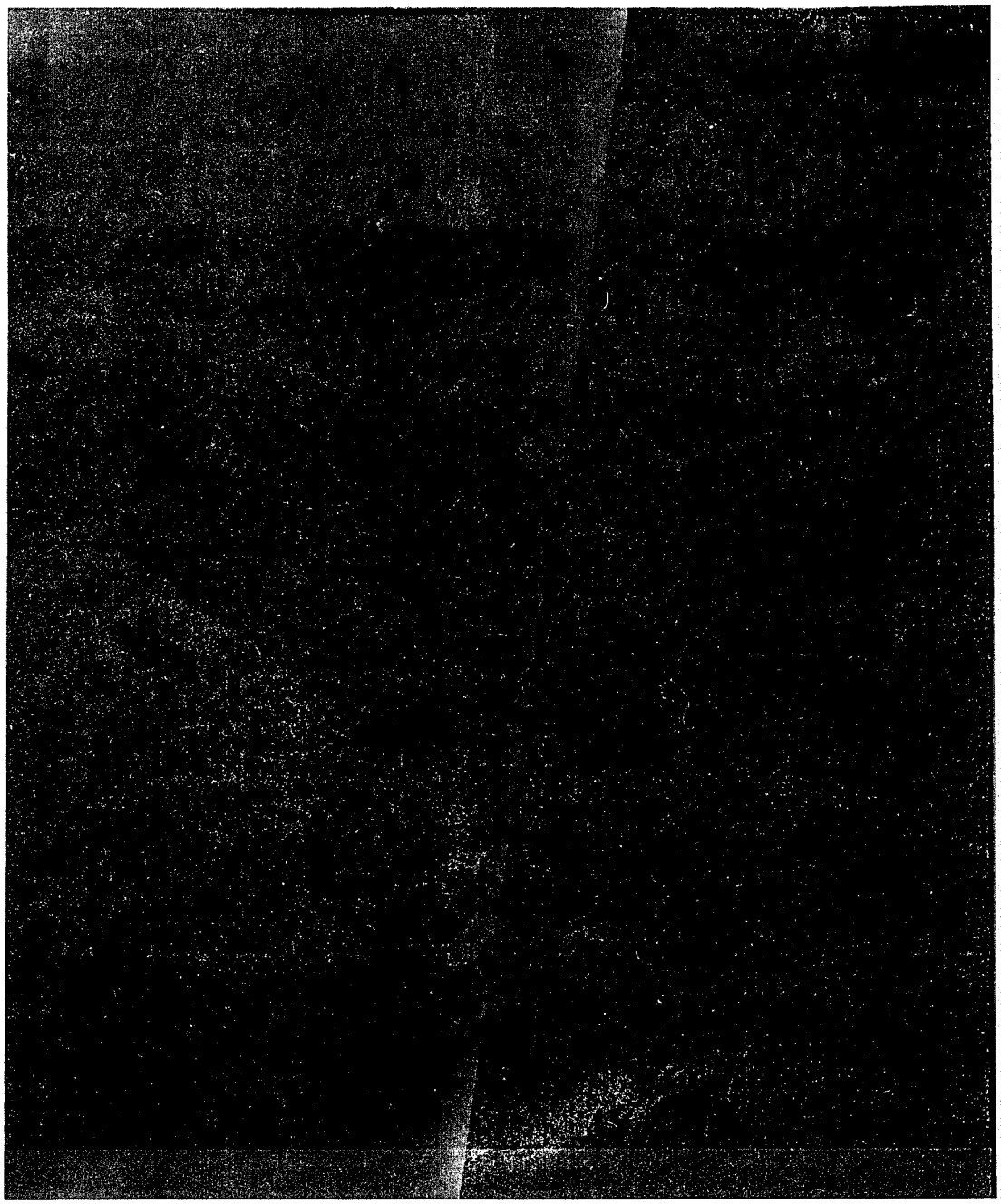
FIG. 6 is a photograph by scanning electron microscope of a portion of the cutting edge of the knife element of FIG. 5, at a magnification of 2700, 100 times the magnification of FIG. 5.

In this connection, a vitreous carbon knife is prepared by first cutting a 1"×1"×¼" square at 45° angle from corner to corner using a standard mechanical diamond saw to form triangles of equal dimensions. Next rough grinding is performed on a standard low speed lapping machine to form the cutting edge. This is a step wise procedure starting with 250 micron diamonds embedded in a metal disk, going down to 15 micron diamonds to achieve a straight, linear edge. Further lapping and polishing is now performed on a standard low speed lapping machine with a further reduction in diamond size, down to 1 micron. The lap used, being made of a soft metal, is prepared in a typical fashion which achieves a straight, linear edge on the vitreous carbon knife. A combination of polishing materials such as silicon oxide and aluminum oxide, together with "carriers" of water, detergents and oils are used to achieve the final edge, FIGS. 5 and 6 are photographs of a knife element produced by the above procedures, which were taken at a magnification of 27 times and 2700 times respectively to show a substantially linear and defect free knife edge. Since all three surfaces of the triangle are lapped and polished, it is possible to produce two cutting edges on one knife, whereas a cleaved vitreous carbon knife only has one cutting edge.

Such procedures may advantageously provide knife edges of substantial length which could be used on histo-logical microtomes which require 25 mm to 38 mm knife lengths or longer; while utilization of fracture procedures tends to limit the maximum knife edge length to the thickness of the carbon plate, which in turn is limited by the vitreous carbon manufacturing process.

Vitreous carbon is a hydrophobic material, and in order to provide for use of the knife edge 38 with water for cleaved sample handling in accordance with conventional sample handling techniques, at least one surface adjacent to the edge may be rendered hydrophilic, although it will be appreciated that such treatment should not substantially degrade the knife edge sharpness.

Hydrophilic properties may be provided by acceptance of the electrostatic charge on the vitreous carbon surface, and in this regard, FIG. 3 illustrates the changing of the surface properties of vitreous carbon knife element 30 by ionization treatment. In this connection, it is important to note that the cutting surface of a vitreous carbon knife must be rendered hydrophilic or it becomes almost impossible to use as a sectioning tool. Due to the physical chemistry of the surface, the vitreous carbon attracts and acquires an electronic charge which renders it hydrophobic and unuseable. Therefore one must deionize the surface, as described below, or use other suitable procedures, which may be utilized to treat the vitreous carbon microtome surface, if desired. As shown in FIG. 3, the preformed knife element 30 may be placed on the stage 42 in an evacuated chamber (e.g., at a vacuum of 150 millitorr) of a vacuum evaporator using a filament voltage to an ionization probe 44 of about 40 volts for 2-5 minutes to render the microtome surface hydrophilic.

In accordance with the present invention, vitreous carbon microtome knives of high sectioning capacity and extreme sharpness may be provided. In this connection, FIG. 4 is a scanning electron microscope photomicrograph of a portion of the knife edge 28 of the microtome knife 20 following cleavage and ionization treatment. The photomicrograph of FIG. 4 is taken at a magnification of 540 times and illustrates the uniformity of the cutting edge, as well as the sharpness of the edge which may be achieved.

In order to demonstrate the performance of the microtome methods and apparatus in accordance with the present invention, a series of sections of various tissue samples and of varying thicknesses are taken over a period of six weeks using a Sorvall ® MT-2B UltraMicrotome in which is mounted a vitreous carbon microtome knife manufactured in accordance with the previous disclosure.

The following table presents the data in connection with various runs:

TABLE 1

SECTIONING RUN WITH HYDROPHOBIC KNIFE ELEMENT
(Knife Not Treated By Ionization)

| Section # | Estimated Section Thickness ($\mu$M) | Section Quality | | |
|---|---|---|---|---|
| | | Acceptable Publisher Quality | Part Acceptable | Unacceptable |
| 1 | Cannot Determine | | | X |
| 2 | Cannot Determine | | | X |
| 3 | Cannot Determine | | | X |
| 4 | Cannot Determine | | | X |
| 5 | Cannot Determine | | | X |
| 6 | Cannot Determine | | | X |
| 7 | Cannot Determine | | | X |
| 8 | Cannot Determine | | | X |
| 9 | Cannot Determine | | | X |
| 10 | Cannot Determine | | | X |

RUN TERMINATED
NOTE:
Due to hydrophobic properties of the knife, quality sections were unattainable.
SPECIMEN TYPE: Anterior angle/animal eye
EMBEDDING MEDIA: Epon (Epoxy resin)

As a comparison, a conventional glass microtome knife is freshly prepared and is used in the microtome. The glass knives are unable to satisfactorily cleave specimens greater than 10 microns in thickness and must frequently be replaced with a new glass knife after taking about 5 full-thickness sections of dimensions in the range of 2-10 microns.

TABLE 2

SECTIONING RUN WITH HYDROPHILIC KNIFE ELEMENT
(Knife Treated By Ionization)

| Section # | Estimated Section Thickness ($\mu$M) | Section Quality | | |
|---|---|---|---|---|
| | | Acceptable Publisher Quality | Part Acceptable | Unacceptable |
| 1 | 4 | X | | |
| 2 | 2 | X | | |
| 3 | 25 | | | X |
| 4 | 10 | | X | |
| 5 | 10 | | X | |
| 6 | 10 | | X | |
| 7 | 10 | X | | |
| 8 | 10 | X | | |
| 9 | 10 | X | | |
| 10 | 10 | X | | |
| 11 | 15 | | X | |
| 12 | 15 | | X | |
| 13 | 15 | | X | |
| 14 | 15 | X | | |
| 15 | 15 | | X | |
| 16 | 25 | | X | |
| 17 | 25 | | X | |

TABLE 2-continued
SECTIONING RUN WITH HYDROPHILIC KNIFE ELEMENT
(Knife Treated By Ionization)

| Section # | Estimated Section Thickness (μM) | Section Quality Acceptable Publisher Quality | Part Acceptable | Unacceptable |
|---|---|---|---|---|
| 18 | 25 | | X | |
| 19 | 15 | X | | |
| 20 | 5 | X | | |
| 21 | 10 | | | X |
| 22 | 10 | X | | |
| 23 | 30 | X | | |
| 24 | 30 | X | | |
| 25 | 15 | X | | |
| 26 | 10 | X | | |
| 27 | 10 | X | | |
| 28 | 10 | X | | |
| 29 | 10 | X | | |
| 30 | 25 | X | | |
| 31 | 25 | X | | |
| 32 | 5 | X | | |
| 33 | 15 | X | | |
| 34 | 20 | X | | |
| 35 | 30 | X | | |
| 36 | 30 | X | | |
| 37 | 30 | X | | |
| 38 | 40 | | X | |
| 39 | 40 | X | | |
| 40 | 40 | X | | |
| 41 | 40+ | X | | |
| 42 | 40+ | X | | |
| 43 | 40+ | X | | |
| 44 | 40 | X | | |
| 45 | 40 | X | | |
| 46 | 40 | X | | |
| 47 | 40 | X | | |
| 48 | 40 | X | | |
| 49 | 40 | X | | |
| 50 | 30 | X | | |
| 50 | 30 | | | |
| 51 | 30 | | X | |
| 52 | 2 | X | | |
| 53 | 50+ | X | | |
| 54 | 1-2 | X | | |
| 55 | 1-2 | X | | |
| 56 | 1-2 | X | | |
| 57 | 1-2 | | X | |
| 58 | 1-2 | X | | |
| 59 | 1-2 | X | | |
| 60 | 1-2 | X | | |
| 61 | 1-2 | X | | |
| 62 | 30 | X | | |
| 63 | 30 | | | X |
| 64 | 30 | | | X |
| 65 | 20 | | X | |
| 66 | 30 | | X | |
| 67 | 30 | X | | |
| 68 | 30 | X | | |
| 69 | 30 | | X | |
| 70 | 30 | X | | |

NOTE:
This knife sample is approximately 5 months old, and will still cleave acceptable samples
SPECIMEN TYPE: Same as in Table 1
EMBEDDING MEDIA: Same as in Table 1

The deterioration of sectioning capability of the glass knives apparently may represent no more than subtle or small scale changes in the knife structure. In this connection, comparison of a scanning electron microscope micrograph, examined at 540x, of a glass knife after failure through use after cleaving 47 specimens of 1000 A—30μ thickness of which time the knife would no longer thin or thick section. Comparison with a similar micrograph of a glass knife, made immediately after cleaving that knife, does not reveal any substantial differences in the edge appearance in the scanning electron micrograph. On the other hand, vitreous carbon knives may have visible edge defects produced through use, and still be capable of cleaving specimen samples.

It will be appreciated by those skilled in the microtomy art that the present disclosure has provided improved methods and apparatus for microtomy.

While the present invention has been particularly described with respect to certain specific embodiments, various modifications, adaptations and variations will be apparent based on the present disclosure, and are intended to be within the spirit and scope of the present invention.

Various of the features of the invention are set forth in the following claims.

What is claimed is:

1. A method for manufacturing a microtome knife element comprising the steps of providing a body of vitreous carbon and forming two smooth absolutely flat, intersecting planar surfaces of said vitreous carbon which intersect at an angle in the range of from about 35° to about 60° along a substantially linear edge having a radius of curvature of less than about 5μ.

2. A method for manufacturing a microtome knife element in accordance with claim 1 wherein said surfaces are formed by providing a vitreous carbon sheet having absolutely flat parallel surfaces, scoring said sheet along a first line, fracturing said sheet along said first line orthogonally to said surfaces to form a first substantially flat cleaved surface, scoring said sheet along a second line intersecting said first line and fracturing said sheet along said second line to form a second substantially flat cleaved surface orthagonally to said sheet surfaces and intersecting said first cleaved surface to form a microtome knife edge.

3. A method in accordance with claim 1 further comprising the step of treating at least one of said planar surfaces adjacent said cleaved plane intersection to render said surface hydrophilic.

4. A method in accordance with claim 1 wherein said treatment comprises deionizing said surface under conditions which do not substantially impair the sharpness of said edge.

5. A method in accordance with claim 1 wherein said intersecting planar surfaces are formed by grinding and polishing of said vitreous carbon body.

6. A method in accordance with claim 1 wherein said vitreous carbon body is reacted with a carbide forming element subsequent to formation of said edge, and yielding a material hardness in excess of 7 and less than 10 on the mohs scale.

7. A microtome knife element comprising a vitreous carbon body having at least two intersecting substantially plane surfaces forming a substantially linear knife edge having a length of at least about 2 millimeters and having a radius of curvature of less than about 5μ.

8. A vitreous carbon microtome knife element in accordance with claim 7 wherein at least one of said intersecting plane surfaces forming said edge is hydrophilic.

9. A vitreous carbon microtome knife element in accordance with claim 7 wherein said plane surfaces intersect at an angle in the range of from about 45° to about 55°.

10. A vitreous carbon microtome knife in accordance with claim 7 wherein said vitreous carbon has a density of at least about 1.35 grams per cm/sq, a permeability of less than $2.5 \times 10^{11}$, a porosity of less than about 0.05%, a compressive strength of at least about 90,000 psi, a tensile strength of at least about 25,000 psi, and a hardness of at least about mohs 7.

* * * * *